US012765792B2

(12) United States Patent
Elbaz et al.

(10) Patent No.: US 12,765,792 B2
(45) Date of Patent: Oct. 20, 2026

(54) NONINVASIVE QUANTITATIVE FLOW MAPPING USING A VIRTUAL CATHETER VOLUME

(71) Applicant: Northwestern University, Evanston, IL (US)

(72) Inventors: Mohammed S. M. Elbaz, Chicago, IL (US); Michael Markl, Chicago, IL (US)

(73) Assignee: Northwestern University, Evanston, IL (US)

( * ) Notice: Subject to any disclaimer, the term of this patent is extended or adjusted under 35 U.S.C. 154(b) by 933 days.

(21) Appl. No.: 17/309,246

(22) PCT Filed: Nov. 12, 2019

(86) PCT No.: PCT/US2019/060856
§ 371 (c)(1),
(2) Date: May 11, 2021

(87) PCT Pub. No.: WO2020/102154
PCT Pub. Date: May 22, 2020

(65) Prior Publication Data

US 2022/0151500 A1 May 19, 2022

Related U.S. Application Data

(60) Provisional application No. 62/760,011, filed on Nov. 12, 2018.

(51) Int. Cl.
*A61B 5/026* (2006.01)
*A61B 6/50* (2024.01)
(Continued)

(52) U.S. Cl.
CPC ............ *A61B 5/0263* (2013.01); *A61B 6/507* (2013.01); *A61B 8/06* (2013.01); *G16H 50/20* (2018.01);
(Continued)

(58) Field of Classification Search
CPC ......... A61B 5/0263; A61B 6/03; A61B 6/503; A61B 6/507; A61B 6/5205; A61B 6/5211;
(Continued)

(56) References Cited

U.S. PATENT DOCUMENTS

| | | | | |
|---|---|---|---|---|
| 2009/0262109 | A1 | 10/2009 | Markowitz | |
| 2011/0107270 | A1 * | 5/2011 | Wang | G16H 20/40 703/11 |

(Continued)

OTHER PUBLICATIONS

Akins CW, et al. Energy loss for evaluating heart valve performance. The Journal of thoracic and cardiovascular surgery 2008;136(4):820-833.

(Continued)

*Primary Examiner* — Christopher L Cook
(74) *Attorney, Agent, or Firm* — Quarles & Brady LLP

(57) ABSTRACT

Described here are systems and methods for generating quantitative flow mapping from medical flow data (e.g., medical images, patient-specific computational flow models, particle image velocimetry data, in vitro flow phantom) over a virtual volume representative of a catheter or other medical device. As such, quantitative flow mapping is provided with reduced computational burdens. Quantitative flow maps can also be generated and displayed in a manner that is similar to catheter-based or other medical device-based mapping, without requiring an interventional procedure to place the catheter or medical device.

48 Claims, 4 Drawing Sheets

(51) Int. Cl.
*A61B 8/06* (2006.01)
*G16H 50/20* (2018.01)
*G16H 50/50* (2018.01)
*G16H 50/70* (2018.01)
*A61B 8/00* (2006.01)

(52) U.S. Cl.
CPC ............ *G16H 50/50* (2018.01); *G16H 50/70* (2018.01); *A61B 8/5261* (2013.01)

(58) Field of Classification Search
CPC ......... A61B 6/563; A61B 8/06; A61B 8/0883; A61B 8/0891; A61B 8/483; A61B 8/488; A61B 8/5207; A61B 8/5215; A61B 8/5261; A61B 8/565; G06T 2207/10076; G06T 2207/10081; G06T 2207/10088; G06T 2207/10116; G06T 2207/10132; G06T 2207/20081; G06T 2207/20084; G06T 2207/30021; G06T 2207/30101; G06T 2207/30104; G06T 2207/30172; G06T 7/0012; G16H 50/20; G16H 50/50; G16H 50/70
See application file for complete search history.

(56) References Cited

U.S. PATENT DOCUMENTS

| | | | | |
|---|---|---|---|---|
| 2011/0144658 | A1* | 6/2011 | Wenderow ............. | G16H 50/50 606/130 |
| 2013/0066219 | A1 | 3/2013 | Jiang | |
| 2015/0045666 | A1 | 2/2015 | Lin | |
| 2015/0063649 | A1 | 3/2015 | Mihalef | |
| 2017/0215836 | A1 | 8/2017 | Yu | |
| 2018/0353241 | A1* | 12/2018 | Tu ........................ | A61B 8/5223 |
| 2020/0167930 | A1* | 5/2020 | Wang ....................... | G06N 3/08 |

OTHER PUBLICATIONS

Barker AJ, et al. Bicuspid aortic valve is associated with altered wall shear stress in the ascending aortaclinical perspective. Circulation: Cardiovascular Imaging 2012;5(4):457-466.
Barker AJ, et al. Viscous energy loss in the presence of abnormal aortic flow. Magnetic resonance in medicine 2014;72(3):620-628.
Bissell MM, et al. Aortic dilation in bicuspid aortic valve disease: flow pattern is a major contributor and differs with valve fusion type. Circulation: Cardiovascular Imaging 2013:CIRCIMAGING. 113.000528.
Bock J, et al. Optimized pre-processing of time-resolved 2D and 3D phase contrast MRI data. Proceedings of the 15th Annual meeting of ISMRM, Berlin, Germany2007.
Bonow RO, et al. 2008 focused update incorporated into the ACC/AHA 2006 guidelines for the management of patients with valvular heart disease: a report of the American College of Cardiology/ American Heart Association Task Force on Practice Guidelines (Writing Committee to revise the 1998 guidelines for the management of patients with valvular heart disease) Endorsed by the Society of Cardiovascular Anesthesiologists, Society for Cardiovascular Angiography and Interventions, and Society of Thoracic Surgeons. Journal of the American College of Cardiology.
Burk J, et al. Evaluation of 3D blood flow patterns and wall shear stress in the normal and dilated thoracic aorta using low-sensitive 4D CMR. Journal of cardiovascular magnetic resonance 2012;14(1):84.
Cibis M, et al. The effect of resolution on viscous dissipation measured with 4D flow MRI in patients with Fontan circulation: Evaluation using computational fluid dynamics. Journal of biomechanics 2015;48(12):2984-2989.
Dyverfeldt P, et al. Magnetic resonance measurement of turbulent kinetic energy for the estimation of irreversible pressure loss in aortic stenosis. JACC: Cardiovascular Imaging 2013;6(1):64-71.
Elbaz MS, et al. Assessment of viscous energy loss and the association with three-dimensional vortex ring formation In left ventricular inflow: In vivo evaluation using four-dimensional flow MRI. Magnetic resonance in medicine 2017;77 (2):794-805.
Garcia J, et al. Volumetric quantification of absolute local normalized helicity in patients with bicuspid aortic valve and aortic dilatation. Magnetic resonance in medicine 2017;78(2):689-701.
Gelpi G, et al. "Bicuspid aortic valve: A complex aortopathy rather than a simple valvulopathy." International journal of cardiology 250 (2018): 120-121.
Guzzardi DG, et al. Valve-related hemodynamics mediate human bicuspid aortopathy: insights from wall shear stress mapping. Journal of the American College of Cardiology 2015;66(8):892-900.
Hassouna MS, et al. Multistencils fast marching methods: A highly accurate solution to the eikonal equation on cartesian domains. IEEE transactions on pattern analysis and machine intelligence 2007;29(9).
Hope Md, et al. 4D flow CMR in assessment of valve-related ascending aortic disease. JACC: Cardiovascular Imaging 2011;4(7):781-787.
Hope Md, et al. Bicuspid aortic valve: four-dimensional MR evaluation of ascending aortic systolic flow patterns. Radiology 2010;255(1):53-61.
Hope Md, et al. Post-stenotic dilation: evaluation of ascending aortic dilation with 4D flow MR imaging. International journal of cardiology 2012;156(2):e40-e42.
Hope TA, et al. Comparison of flow patterns in ascending aortic aneurysms and volunteers using four-dimensional magnetic resonance velocity mapping. Journal of Magnetic Resonance Imaging: An Official Journal of the International Society for Magnetic Resonance in Medicine 2007;26(6):1471-1479.
Hyslop NP, et al. Estimating precision using duplicate measurements. Journal of the Air & Waste Management Association 2009;59(9):1032-1039.
International Searching Authority. International Search Report and Written Opinion for application PCT/US2019/060856. Mailed on Jan. 22, 2020. 13 pages.
Kamphuis V, et al. Disproportionate Intraventricular Viscous Energy Loss in Fontan Patients: analysis by 4D Flow MRI. European Heart Journal-Cardiovascular Imaging 2018.
Kamphuis VP, et al. Scan-rescan reproducibility of diastolic left ventricular kinetic energy, viscous energy loss and vorticity assessment using 4D flow MRI: analysis in healthy subjects. The international journal of cardiovascular imaging 2018:1-16.
Mahadevia R, et al. Bicuspid aortic cusp fusion morphology alters aortic three-dimensional outflow patterns, wall shear stress, and expression of aortopathy. Circulation 2014;129(6):673-682.
Maurer CR, et al. A linear time algorithm for computing exact Euclidean distance transforms of binary images in arbitrary dimensions. IEEE Transactions on Pattern Analysis and Machine Intelligence 2003;25(2):265-270.
Myles P, et al. I. Using the Bland-Altman method to measure agreement with repeated measures. British Journal of Anaesthesia, vol. 99, Issue 3, Sep. 2007, pp. 309-311.
Nishimura RA, et al. 2014 AHA/ACC guideline for the management of patients with valvular heart disease: a report of the American College of Cardiology/American Heart Association Task Force on Practice Guidelines. The Journal of Thoracic and Cardiovascular Surgery 2014;148(1):e1-e132.
Saikrishnan N, et al. Bicuspid aortic valves are associated with increased wall and turbulence shear stress levels compared to trileaflet aortic valves. Biomechanics and modeling in mechanobiology 2015;14(3):577-588.
Sievers H-H, et al. A classification system for the bicuspid aortic valve from 304 surgical specimens. The Journal of thoracic and cardiovascular surgery 2007;133(5):1226-1233.
Siu SC, et al. Bicuspid aortic valve disease. Journal of the American College of Cardiology 2010;55(25):2789-2800.
Soille P. Morphological image analysis: principles and applications: Springer Science & Business Media, 2013: Chapter 7, p. 219-221.
Tao Q, et al. Deep learning-based method for fully automatic quantification of left ventricle function from cine MR mages: a multivendor, multicenter study. Radiology 2018;290(1):81-88.

(56) References Cited

OTHER PUBLICATIONS

Verma S, et al. Aortic dilatation in patients with bicuspid aortic valve. New England Journal of Medicine 2014;370 (20):1920-1929.
Verma S, et al. Knowledge, attitudes, and practice patterns in surgical management of bicuspid aortopathy: a survey of 100 cardiac surgeons. The Journal of thoracic and cardiovascular surgery 2013;146(5):1033-1040. e1034.
Yu Z, et al. A segmentation-free approach for skeletonization of gray-scale images via anisotropic vector diffusion. Proceedings of the 2004 IEEE Computer Society Conference on Computer Vision and Pattern Recognition, 2004 CVPR 2004: IEEE, 2004; p. I-I.

* cited by examiner

NONINVASIVE QUANTITATIVE FLOW MAPPING USING A VIRTUAL CATHETER VOLUME

CROSS-REFERENCE TO RELATED APPLICATIONS

This application represents the U.S. national stage entry of International Patent Application Serial No. PCT/US2019/060856, filed on Nov. 12, 2019, and claims the benefit of U.S. Provisional Patent Application Ser. No. 62/760,011, filed on Nov. 12, 2018, both entitled "NONINVASIVE QUANTITATIVE FLOW MAPPING USING A VIRTUAL CATHETER VOLUME," the contents of each of which are herein incorporated by reference in their entirety for all purposes.

BACKGROUND

Invasive diagnostic catheterization remains the gold standard for hemodynamic assessment for clinical decision making in several freely occurring and common heart valve diseases (e.g., bicuspid aortic valve ("BAV"), valve stenosis, valve insufficiency/regurgitation) and vascular diseases (e.g., coarctation, peripheral artery disease ("PAD"), cerebral aneurysms, brain arteriovenous malformation). Nonetheless, hemodynamic evaluation by conventional invasive catheterization is substantially limited by its inherently invasive nature and associated risk for procedural complications, as well as high cost and health care utilization. Moreover, invasive catheterization does not provide information on other clinically important measures, such as regional blood flow or flow patterns, which are increasingly associated with the development of various cardiovascular and neurovascular diseases.

Several imaging modalities (e.g., MRI, Doppler echocardiography), patient-specific computational flow modeling (CFD, CFD-assisted flow CT), and in vitro systems (e.g., particle image velocimetry, flow phantom) can provide noninvasive blood flow information, but there remains a need for the intuitive visualization and quantification of cardiovascular or neurovascular blood flow comparable to the gold standard invasive diagnostic catheterization for hemodynamic evaluation.

SUMMARY OF THE DISCLOSURE

The present disclosure addresses the aforementioned drawbacks by providing a method for generating a flow metric map from medical flow data. The method includes providing medical flow data to a computer system and segmenting the medical flow data to generate a segmented volume corresponding to a region-of-interest. A reference point within the segmented volume is determined and a virtual volume is constructed as a subvolume within the segmented volume and defined relative to the reference point. Masked medical flow data are generated by masking the medical flow data using the virtual volume, and at least one flow metric is computed based on the masked medical flow data. A flow metric map is then generated using the at least one flow metric.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
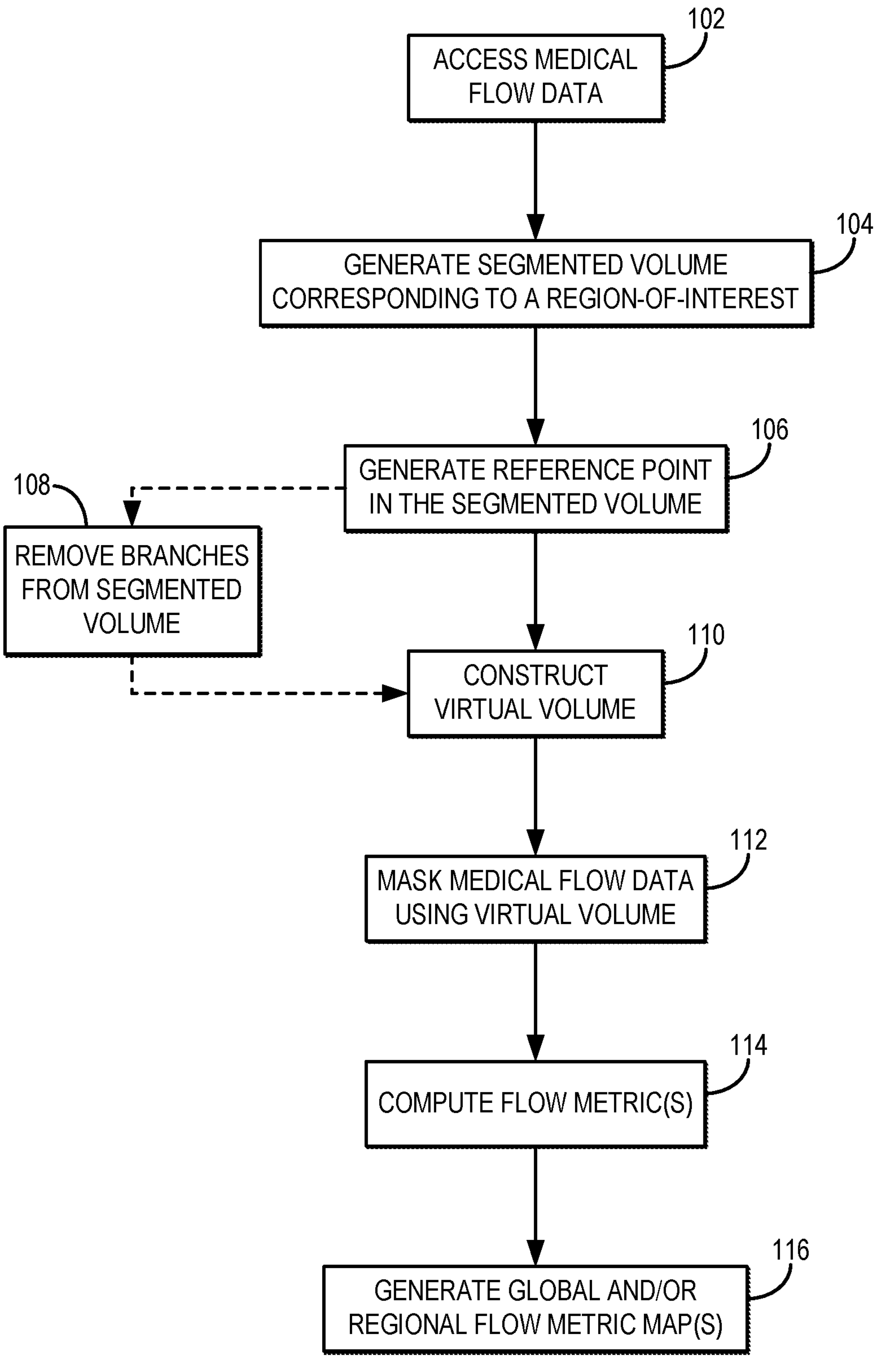
FIG. 1 is a flowchart setting forth the steps of an example method for generating flow metric maps over a virtual volume, such as a virtual volume associated with a catheter or other medical device.

Described here are systems and methods for generating quantitative flow mapping from medical flow data (e.g., medical images, patient-specific computational flow models, in vitro phantoms, particle image velocimetry data) over a virtual volume representative of a catheter or other medical device. As such, the systems and methods described in the present disclosure provide quantitative flow mapping with reduced computational burdens, and are able to generate and display this flow mapping in a manner that is similar to catheter-based or other medical device-based mapping without requiring an interventional procedure to place the catheter or medical device.

In addition to enabling noninvasive quantification of conventional catheter-derived hemodynamics or other flow metrics, the systems and methods described in the present disclosure enable flexible quantitative mapping and visualization of different global and regional hemodynamic, or other flow, metrics that can be derived from the velocity field. For instance, metrics such as pressure gradients, pressure fields, kinetic energy, energy loss, turbulent kinetic energy, flow velocity histograms, and flow patterns (e.g., helicity, vorticity, vortex flow, helical flow, organized flow patterns, disorganized flow patterns) can be generated. The systems and methods described in the present disclosure also allow a high degree of automation.

The systems and methods described in the present disclosure are applicable to different noninvasive flow imaging modalities, such as magnetic resonance imaging ("MRI"), ultrasound Doppler echocardiography, and so on. Quantitative flow metrics, such as hemodynamic metrics, can be computed in a virtual volume that is representative of an invasive device, such as a catheter, endoscope, or other interventional or invasive medical device. As such, medical device-like flow metric quantification can be achieved from noninvasive imaging modalities that provide velocity field information.

As opposed to measuring flow with invasive medical devices, the systems and methods described in the present disclosure can be virtually applied to the assessment of flow metrics in any subject as long as noninvasive velocity field data, or other flow data, can be acquired from a suitable medical imaging modality, or flow modeling or simulations (e.g., using computational flow dynamics). The resemblance of the generated flow metric maps to invasive catheter, or other medical devices, makes interpretation of the virtual volume-derived flow metrics readily intuitive to clinicians.

In this way, the systems and methods described in the present disclosure enable clinicians to visualize and otherwise interpret medical flow data in a familiar way without having to perform an invasive procedure in order to obtain and process that medical flow data.

Advantageously, the systems and methods described in the present disclosure provide simultaneous evaluation of conventional invasive catheter hemodynamics and an array of three-dimensional ("3D") time-resolved hemodynamic parameters or metrics not able to be measured or quantified using interventional medical devices (e.g., kinetic energy, energy loss, helicity, vorticity). Moreover, multiple different flow metrics can be computed within a single processing workflow, enabling flexible quantification of multiple different flow metric or hemodynamics that can be evaluated from the velocity field or other flow data.

The systems and methods described in the present disclosure provide a high degree of automation, which enables fast and reproducible analysis of large patient cohorts. In vivo-like flow evaluation from patient-specific computational fluid dynamics models are also capable, thereby facilitating precision medicine.

As one non-limiting example, the systems and methods described in the present disclosure enable noninvasive quantification of global and regional cardiovascular blood flow hemodynamics and flow patterns and can therefore be used to assess disease severity or risk of disease development. As noted, the generated flow metric maps can also provide intuitive visualization and quantification of otherwise complex global and regional cardiovascular blood flow patterns, the intuitive visualization of in vivo blood flow data acquired by MRI techniques (e.g., 4D flow MRI, flow-sensitive MRI), the intuitive visualization of in vivo blood flow data acquired by echocardiography (e.g., Doppler echo, Doppler transesophageal echocardiography, Doppler 3D echo), and so on.

The systems and method described in the present disclosure also enable noninvasive quantification of global and regional neurovascular hemodynamics and can therefore be used to assess disease severity or risk of disease development. As noted, the generated flow metric maps can also provide an intuitive visualization of global and regional neurovascular blood flow and hemodynamic patterns.

By enabling quantification and visualization of blood flow hemodynamics from patient-specific cardiovascular and neurovascular computational fluid dynamics ("CFD") simulations, the systems and methods described in the present disclosure can also provide for precision medicine applications.

Referring now to FIG. 1, a flowchart is illustrated as setting forth the steps of an example method for generating a virtual volume and computing flow metrics over the virtual volume, which may correspond to a virtual catheter or other virtual medical device. The method includes accessing medical flow data with a computer system, as indicated at step 102. The medical flow data can be accessed with the computer system by accessing or otherwise retrieving stored medical flow data from a memory or other suitable data storage device or media. The medical flow data can also be accessed with the computer system by acquiring medical flow data with a medical imaging system and communicating the medical flow data to the computer system, which may in some instances be a part of the medical imaging system.

In general, the medical flow data contain medical images, but in some instances may include raw data acquired with a medical imaging system, images generated from medical images (e.g., parameter maps that depict quantitative parameters computed from medical images), or patient-specific computational flow modeling data (e.g., CFD data, CFD-assisted flow CT). The medical flow data preferably contain images or data that depict or otherwise provide information about flow (e.g., blood flow, cerebrospinal fluid flow) in a subject. In some instances, the flow information may include flow velocity data, such as flow velocity field data. The medical flow data may be one-dimensional data or multidimensional data. The medical flow data may also contain data associated with a single time point, multiple time points, or a period of time.

The medical flow data can include images acquired with a magnetic resonance imaging ("MRI") system, an ultrasound system, or another suitable medical imaging system, including medical imaging systems capable of in vivo imaging, in vitro imaging, or both. For instance, the medical flow data can include magnetic resonance images that depict blood flow in a subject's vasculature, or Doppler ultrasound images that depict blood flow in a subject's vasculature. The magnetic resonance images can be four-dimensional ("4D") blood flow images that depict or otherwise provide information about three-dimensional ("3D") blood flow over a period of time. As one non-limiting example, the 4D blood flow images may provide information about blood flow velocities over a cardiac cycle. The Doppler ultrasound images can be 3D Doppler echocardiography images that depict of otherwise provide information about 3D blood flow in the subject.

The medical flow data are then segmented to generate a segmented volume corresponding to a region-of-interest ("ROI"), as indicated at step 104. The ROI may correspond to an anatomical region, a compartment, an organ-of-interest, or the like. The medical flow data may be segmented using any suitable algorithm or technique for segmentation, including model-based methods such as artificial intelligence model-based methods, machine learning-based methods, and other trained mathematical model-based methods. As one non-limiting example, a model-based method can include deep learning-based methods such as those described by Q. Tao, et al., in "Deep Learning-Based Method for Fully Automatic Quantification of Left Ventricle Function from Cine MR Images: a Multivendor, Multicenter Study," *Radiology,* 2018; 290(1):81-88, which is herein incorporated by reference in its entirety. In other non-limiting examples, suitable machine learning algorithms can also be used, including neural network-based algorithms that are trained to segment input medical flow data.

As one non-limiting example, the ROI may correspond to a portion of the subject's vasculature. The portion of the subject's vasculature may include the aorta. In other instances, the portion of the subject's vasculature may include the aorta and branch arteries connected to the aorta. In still other instances, the portion of the subject's vasculature may include one or more components of the subject's vasculature, including one or more components of the cerebral vasculature, the carotid arteries, or peripheral vasculature. As another non-limiting example, the ROI may include the subject's heart or components thereof. For instance, the ROI may encompass the entire heart, one or more chambers of the heart, one or more valves, and so on.

After the segmented volume corresponding to the ROI has been generated, one or more reference points corresponding to the segmented volume are generated, as indicated at step 106. In some examples, the reference point can include a centerline of the segmented volume or another linear or curvilinear path extending through all or a part of the segmented volume. For instance, the centerline, or other linear or curvilinear path, can be generated by inputting the segmented volume to a curve detection algorithm in order to generate the centerline or other linear or curvilinear path. As one example, the curve detection algorithm may include a fast-marching method. In some other examples, the curvilinear path (e.g., a centerline) can also be computed using a segmentation-free method, such as those described by Z. Yu and C. Bajaj, in "A Segmentation-Free Approach for Skeletonization of Gray-Scale Images via Anisotropic Vector Diffusion," *Proceedings of the* 2004 *IEEE Computer Society Conference on Computer Vision and Pattern Recognition,* 2004; CVPR: IEEE 2004, pp. 415-420, which is herein incorporated by reference in its entirety. In these instances, the centerline (or other reference point or points) can be computed without first segmenting the medical flow data.

In some other examples, the reference point can include a center point or another point of reference within the segmented volume (e.g., a point associated with an anatomical landmark, a point associated with a fiducial marker, a user-selected point within the segmented volume, a point associated with a flow descriptor). In still other examples, the reference point can include a geometry reference, such as a geometric shape constructed in the segmented volume. The geometric shape may be constructed by a user. For instance, the geometric shape can be constructed by connecting a plurality of user-selected points. The geometric shape can thus be a point, a line, a plurality of connected line segments, a polygon, and so on. The lines or line segments may include one or more straight lines, one or more curvilinear lines, one or more curves, or combinations thereof.

When the segmented volume includes branches (e.g., branches of the vasculature) that are not of interest, it may be desirable to remove these branches from the volume. In these instances the segmented volume can optionally be processed to remove the branches, as indicated at step 108. It will be appreciated that in some implementations, the branches can also be removed from the segmented volume before the reference point is generated in step 106.

Based on the segmented volume and the reference point, a virtual volume is constructed, as indicated at step 110. The virtual volume can be constructed by defining a geometry of the virtual volume. For instance, the virtual volume can be constructed by computing one or more radii that define the outer extent of a tubular virtual volume. The tubular virtual volume can have a single radius centered on the reference point (e.g., centerline, center point), or can have variable radii along the length of the tubular virtual volume (e.g., along the length of the centerline). In these instances, the virtual volume can be constructed as a 3D tube with the corresponding fixed radius or variable radii.

As one example, a radius can be determined by computing a distance measure between the reference point and a point on the segmented volume. The distance measure can be a non-Euclidean distance. For instance, the distance measure can be computed based on a geodesic distance transform, or the like. In some other instances, the distance measure can be a Euclidean distance. For instance, the distance measure can be computed based on a 3D distance transform, or the like. In some examples, a 3D distance map can be computed based on the segmented volume and the reference point, and the 3D distance map can be used to compute one or more radii. For instance, a geodesic distance map can be generated by computing voxel-wise distances between the reference point and voxels associated with the lumen (e.g., vessel wall, wall of the tubular structure) using a 3D geodesic distance transform.

As one non-limiting example, the radius of a tubular virtual volume can be selected based on a percentile ranked radius of multiple radii computed relative to the reference point (e.g., multiple radii computed along the centerline). For instance, the radius can be selected based on the 75th percentile of radii along the centerline using a 3D Euclidean transform, or other suitable distance measure. Multiple radii can also be selected based on multiple selection criteria, thresholding criteria (e.g., all radii above a certain threshold, below a certain threshold, or within a range of selected thresholds), and so on.

In the case of using a geodesic distance map, this criterion can be represented as, $$R = \frac{P75(GDM)}{\gamma}, \text{ with } \gamma > 0[\text{voxels or mm}]; \quad (1)$$

where P75(GDM) is the 75th percentile of all distances in a geodesic distance map, and $\gamma$ is a positive real number that adjusts the virtual volume radius, R, as a fraction of the individual tubular organ (e.g., aorta, other blood vessel, esophagus, or other tubular organ) size, volume, or both. This parameter, $\gamma$, allows the fractional virtual volume size relative to the tubular organ volume to be equivalent among different subjects for systematic comparison. The parameter, $\gamma$, can also define a margin distance of the virtual volume from the lumen of the tubular organ (i.e., larger values of $\gamma$ allow a larger margin from the tubular organ lumen boundary and vice versa). As one non-limiting example, the parameter $\gamma$ can be selected from the range of $\gamma=1$ to $\gamma=5$. In some implementations, $\gamma$ can be selected as $\gamma=3$.

The choice of the $\gamma$ parameter can be made based on the pathology or potential pathology under examination, and the type and extent of flow details to be captured. For capturing flow near the lumen wall, values of $\gamma$ close to 1 (i.e., a larger relative radius) may be more advantageous, while $\gamma>1$ (i.e., a smaller relative radius) may be more advantageous for capturing flow details near the center of the tubular organ. In medical flow data with high lumen wall motion, $\gamma>1$ may also help to position the virtual volume with a sufficient margin from the dynamic wall boundary to mitigate associated errors. When comparison flow metrics across multiple subjects, the same $\gamma$ model should be used across the study participants.

The virtual volume can also be constructed based on the flow information, or other information, available in the medical flow data. For example, the virtual volume can be constructed based on a thresholding of the flow information available in the medical flow data. In such instances, the virtual volume can be defined as the regions of the segmented volume corresponding to flow velocity information in the medical flow data that satisfy one or more thresholding criteria. As an example, high flow regions can be assigned to the virtual volume, such that those regions in the medical flow data having flow velocities above a certain threshold are added to the virtual volume. As another example, the virtual volume can be constructed based on a region growing using the reference point as an initial seed for the region. The region growing can proceed based on image intensity values, flow data values, or the like. Region growing can be implemented over a single region or over multiple regions. As another example, the virtual volume can be constructed based on flow information on the stream direction or flow path(s), which may be contained in or generated from the medical flow data. For instance, the virtual volume can be constructed using flow streamlines, path lines, or the like (at one time point or over a period of time).

After the virtual volume is constructed, it can be refined or otherwise updated. For instance, the virtual volume can be refined based on user interaction, or using an automated or semi-automated process. In such instances, the virtual volume can be adjusted to include or exclude regions based on the user interaction or based on automated criteria.

In some alternative implementations, the virtual volume can be constructed directly from the medical flow data using a suitably trained machine learning algorithm. In these instances, the medical flow data are input to a trained machine learning algorithm, generating output as the virtual volume. The machine learning algorithm can implement a neural network, such as a convolutional neural network or a residual neural network, or other suitable machine learning algorithm. In some example, the machine learning algorithm can implement deep learning. The machine learning algorithm can be trained on suitable training data, such as medical flow data that have been segmented and/or labeled, corresponding reference point data, and so on.

The medical flow data are then masked using the virtual volume, as indicated at step 112. For instance, the medical flow data can be masked by the virtual volume at each acquired time point, resulting in time-resolved (or single time point) flow data (e.g., flow velocity field data) within the virtual volume. As a result, flow metrics can be computed over the more limited virtual volume, which may correspond to a subvolume within the segmented volume. Computing flow metrics over this virtual volume this helps ensure that the time-resolved flow data used for the calculations do not extend beyond the anatomy, even when the underlying anatomy is moving from one time frame to the next. In some instances, the virtual volume can be constructed such that it defines a percent of consistent flow data, a margin of reliable flow data, or the like.

One or more metrics can be computed from the masked medical flow data, as indicated at step 114. For each time point, various flow metrics can be quantified based on the masked flow information in the virtual volume. As one example, the flow metrics may be one or more hemodynamic metrics, such as kinetic energy, energy loss, turbulent kinetic energy, pressure gradients, pressure maps, flow velocity histograms, or flow patterns (e.g., helicity, vorticity, vortex flow, helical flow, organized flow patterns, disorganized flow patterns).

As one non-limiting example, one or more vorticity metrics can be computed from the masked medical flow data. For instance, if u, v, and w denote the three velocity field components acquired from medical flow data (e.g., 4D Flow MRI or other medical flow data) over the principal velocity directions x, y, and z, respectively, then the vorticity $\omega_{i,t}$ at voxel i of an acquired time point t can be given as, $$\omega_{i,t} = \left(\frac{\partial w_{i,t}}{\partial y_{i,t}} - \frac{\partial v_{i,t}}{\partial z_{i,t}}, \frac{\partial u_{i,t}}{\partial z_{i,t}} - \frac{\partial w_{i,t}}{\partial x_{i,t}}, \frac{\partial v_{i,t}}{\partial x_{i,t}} - \frac{\partial u_{i,t}}{\partial y_{i,t}}\right)[1/s]. \tag{2}$$

Partial derivatives can be computed using a finite difference method (e.g., central difference) or other suitable technique. Then, the volume-normalized integral sum of vorticity over the virtual volume at an acquired time phase, t, in per second(s) can be computed as, $$V_{vorticity} = \frac{\sum_{i=1}^{M} |\omega_{i,t}| L_{i,t}}{M \times L_{i,t}} [1/s]; \tag{3}$$

where $|\omega_{i,t}|$ is the magnitude of the vorticity vector, M is the total number of voxels in the virtual volume, and $L_{i,t}$ is the voxel volume in liters.

As another non-limiting example, one or more viscous energy loss metrics can be computed from the masked medical flow data. For instance, Given an acquired velocity field, v, the rate of viscous energy loss, $\dot{E}L$, in watts (W) and the total energy loss, $EL_{total}$, in joules (J) over a given period of time, T, can be computed from medical flow data (e.g., 4D Flow MRI or other medical flow data) using the viscous dissipation function, $\Phi_v$, in the Newtonian Navier-Stokes energy equations:

$$\Phi_v = \frac{1}{2}\sum_{i=1}^{3}\sum_{j=1}^{3}\left(\left(\frac{\partial v_i}{\partial x_i} + \frac{\partial v_j}{\partial x_j}\right) - \frac{2}{3}(\nabla \cdot v)\delta_{ij}\right)^2, \tag{4}$$

$$\begin{cases} \delta_{ij} = 1, & \text{if } i = 1 \\ \delta_{ij} = 0, & \text{if } i \neq j \end{cases} [s^{-2}];$$

where $\Phi_v$ represents the rate of viscous energy dissipation per unit volume; i and j correspond to the velocity directions, x, y, and z; and $\nabla \cdot v$ denotes the divergence of the velocity field. The instantaneous volume-normalized total viscous energy loss rate over the volume in Watt/m$^3$ at an each acquired time phase can be computed as:

$$EL = \frac{\mu \sum_{i=1}^{M} \Phi_v L_i}{M \times L_i} [W/m^3]; \tag{5}$$

assuming the blood, or other fluid associated with the medical flow data, as a Newtonian fluid, the dynamic viscosity can be $\mu$=0.004 Pa·s, and where M is the total number of voxels in the virtual volume and $L_i$ is the voxel volume in m$^3$.

As still another non-limiting example, one or more kinetic energy metrics can be computed from the masked medical flow data. For instance, For each acquired time point, the total volume-normalized kinetic energy over the virtual volume (KE) can be computed as, $$KE = \frac{\sum_{i=1}^{M} \frac{1}{2} m V^2}{M \times L_i} [J/m^3]; \tag{6}$$

where m is the mass representing the voxel volume multiplied by the density of blood (1.025 g/ml) or other fluid associated with the medical flow data; V is the 3-directional velocity from the medical flow data (e.g., 4D Flow MRI or other medical flow data); M is the total number of voxels in the virtual volume; and $L_i$ is the voxel volume in m$^3$.

In some implementations, volumetric intra-lumen flow dynamics (e.g., intra-aortic hemodynamics) can be quantified. For instance, the instantaneous volumetric total sum for each of kinetic energy, viscous energy loss rate, and vorticity over the cardiac cycle can be computed. In some other implementations, peak kinetic energy, peak viscous energy loss rate, and/or peak vorticity can be calculated and normalized by the corresponding virtual volume.

A global map, regional map, or both, of the one or more metrics can then be generated over the larger volume, as indicated at step 116. For example, the metrics can be integrated over the volume to generate a global map, or a regional map of the flow metrics can be generated. In either instance, the global or regional flow metric maps can be displayed to a user or stored for later use or processing. For example, the flow metric maps can be displayed to a user using a display or a user interface, which may be a graphical user interface that is configured to display flow metric maps alone or together with the medical flow data or other images of the subject.

In an example study, a virtual catheter ("vCath") was demonstrated in bicuspid aortic valve ("BAV") patients. BAV is one of the most common congenital heart defects, affecting up to two percent of the population, and is responsible for more deaths and complications than all other congenital heart defects combined. The vCath technique was successfully employed for evaluating longitudinal changes in 3D kinetic energy and viscous energy loss in the blood flow over systole of 44 BAV patients. A total of 123 4D flow MRI scans were analyzed between healthy controls and patients. The quantitative time-varying volumetric information enabled by the 4D flow vCath identified significant changes in longitudinal aortic hemodynamic in BAV patients characterized by lower 3D systolic kinetic energy ($p=0.03$) and higher viscous energy loss ($p=0.04$) relative to baseline and healthy controls studied. In 109 (out of 123) analyzed scans, the vCath analysis was automated, making it suited for analyzing large cohorts and efficient translation into clinical workflows.

Figure 2:
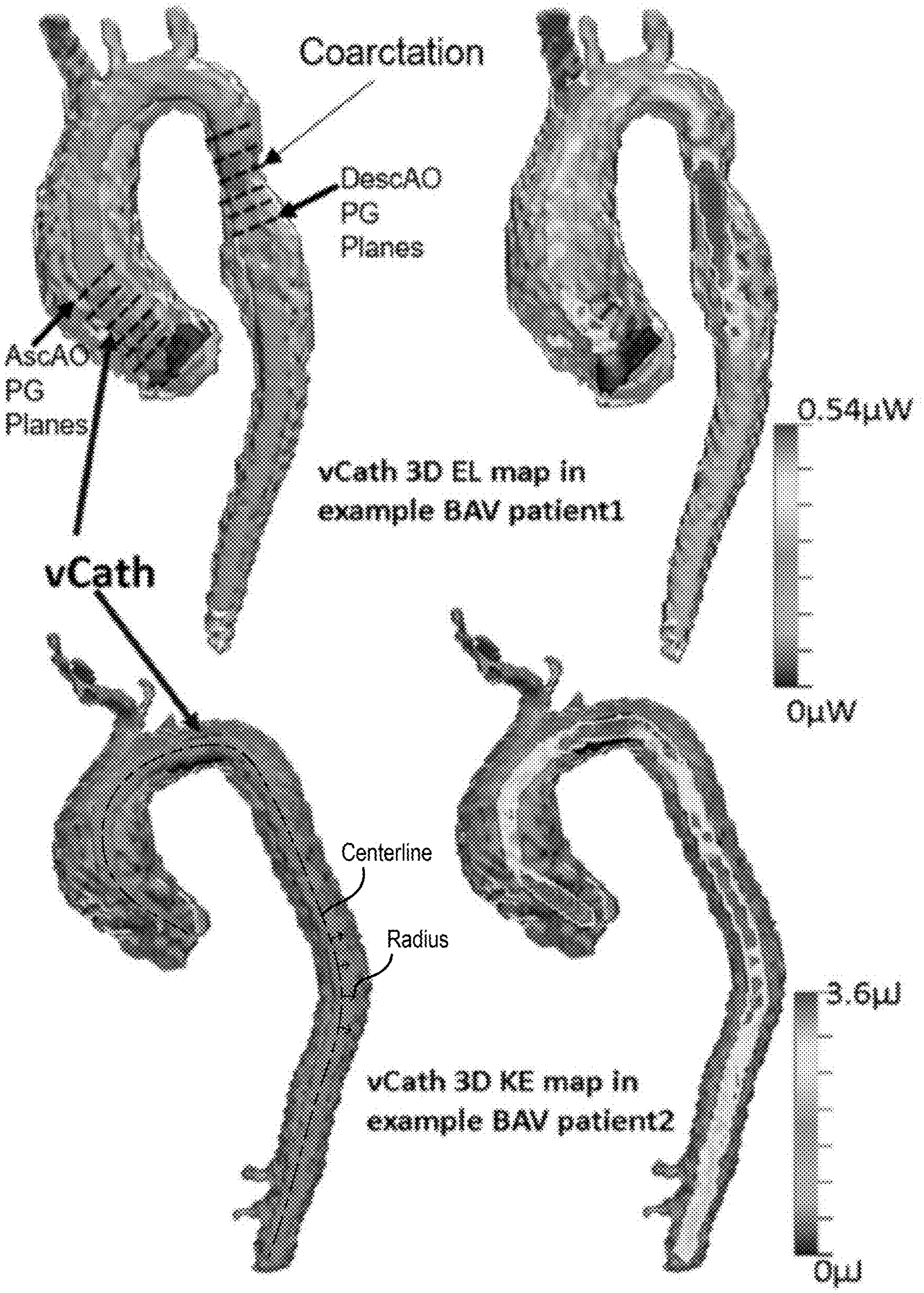
FIG. 2 shows example virtual catheter results of energy loss ("EL") and kinetic energy ("KE") maps at peak systole in two different bicuspid aortic valve ("BAV") patients.

Furthermore, noninvasive vCath-estimated pressure gradient ("PG") was validated against gold standard invasive cardiac catheterization in an example study. PG is an important conventional clinical marker of aortic and valvular disease severity. In particular, systolic PG between Ascending Aorta ("AscAO") and Descending Aorta ("DescAO") was evaluated in two BAV patients with aortic coarctation (narrowing of the aorta) located proximal to the descending aorta. Examples of kinetic energy and energy loss maps generated over a virtual catheter volume are shown in FIG. 2.

The systems and methods described in the present disclosure provide for a reproducible 4D virtual catheter technique for the systematic evaluation of intra-aortic volumetric hemodynamics, including viscous energy loss, kinetic energy, and vorticity. As described above, other fluid and flow dynamics can also be generated in other tubular organs, such as blood vessels other than the aorta, the esophagus, and suitable tubular structures.

It is a challenge to measure and assess intra-aortic hemodynamics (and flow dynamics in other tubular organs) from medical flow data given variations in the size and shape of the aorta or other tubular organ among different individuals, disease stages, and even during healthy aging of the same individual. Advantageously, the systems and methods described in the present disclosure can automatically adapt to each subject-specific anatomy shape and size to ensure reliable subject-specific evaluation and systematic comparison among subjects.

In some implementations, this automated subject-specific personalization can be achieved by using a volumetric geodesic distance map, a 3D centerline, and the γ parameter. The centerline captures the skeleton of the subject-specific tubular organ shape and provides a consistent starting point between different subjects. The 3D geodesic distance map captures the volumetric tubular organ size and morphology over the subject's specific tubular organ volume. The γ parameter allows for the virtual volume radius to be systematically and automatically derived as a fraction of each subject-specific tubular organ size, instead of an arbitrary absolute or constant radius over all subjects. Adjusting the γ parameter also provides the flexibility of systematically defining and studying varying volumetric fractions of the intra-tubular organ volume along the centerline.

Figure 3:
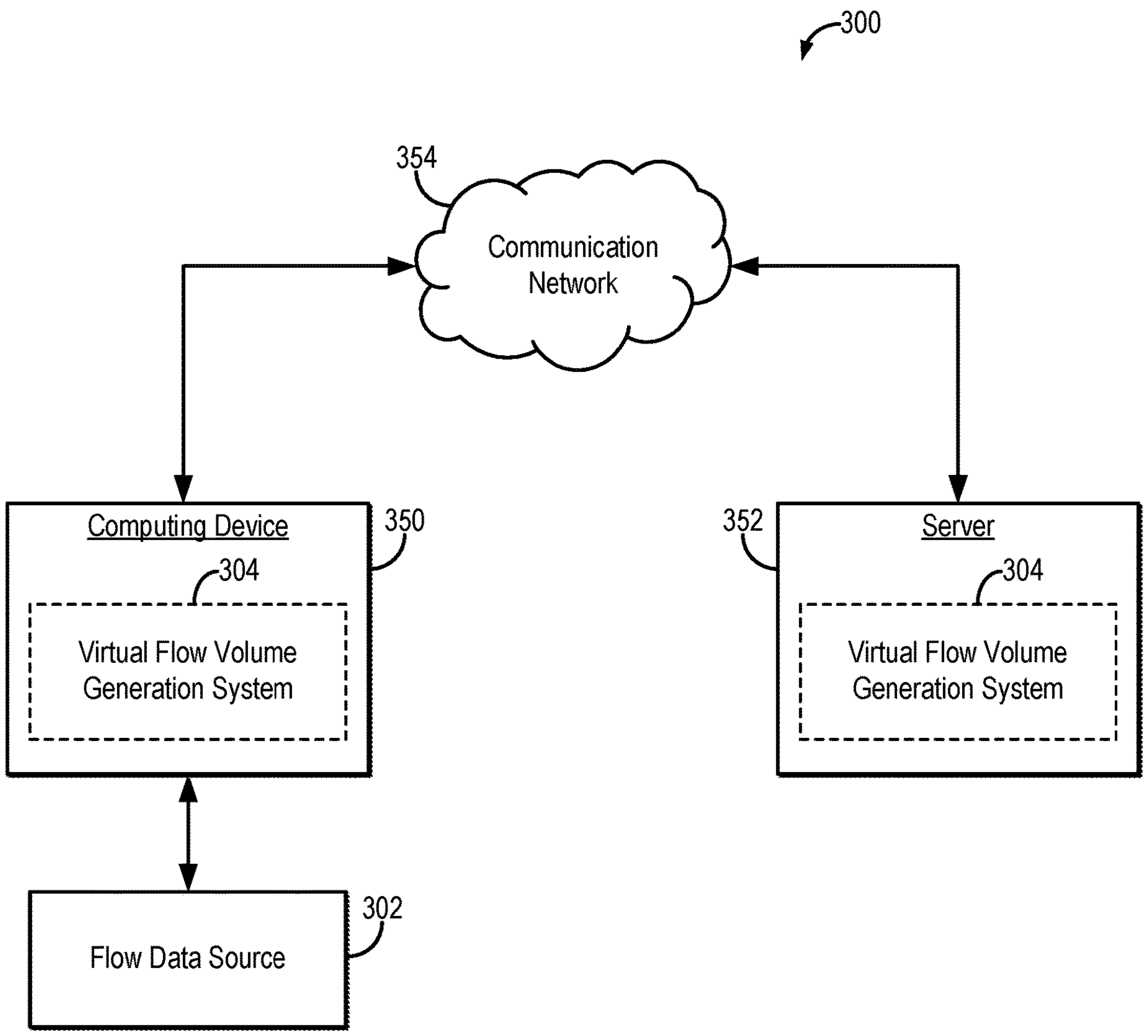
FIG. 3 is a block diagram of an example system for generating a virtual volume and computing flow metrics over the virtual volume.

Referring now to FIG. 3, an example of a system 300 for generating a virtual volume and computing flow metrics over the virtual volume, in accordance with some embodiments of the systems and methods described in the present disclosure, is shown. As shown in FIG. 3, a computing device 350 can receive one or more types of data (e.g., medical flow data) from flow data source 302. As one example, the flow data source 302 may be a medical image source, such as a magnetic resonance imaging ("MRI") system or image source, a computer tomography ("CT") system or image source, an x-ray imaging system or image source, an ultrasound system or image source, and so on. As another example, the flow data source 302 may be a flow simulation source, a particle image velocimetry ("PIV") source, an in vitro phantom source, a computational fluid dynamics ("CFD") source, and so on. In some embodiments, computing device 350 can execute at least a portion of a virtual flow volume generation system 304 to generate a virtual volume and to compute flow metrics from data received from the flow data source 302.

Additionally or alternatively, in some embodiments, the computing device 350 can communicate information about data received from the flow data source 302 to a server 352 over a communication network 354, which can execute at least a portion of the virtual flow volume generation system 304 to generate a virtual volume and to compute flow metrics from data received from the flow data source 302. In such embodiments, the server 352 can return information to the computing device 350 (and/or any other suitable computing device) indicative of an output of the virtual flow volume generation system 304 to generate a virtual volume and to compute flow metrics from data received from the flow data source 302.

In some embodiments, computing device 350 and/or server 352 can be any suitable computing device or combination of devices, such as a desktop computer, a laptop computer, a smartphone, a tablet computer, a wearable computer, a server computer, a virtual machine being executed by a physical computing device, and so on. The computing device 350 and/or server 352 can also reconstruct images from the data.

In some embodiments, flow data source 302 can be any suitable source of medical flow data (e.g., measurement data, images reconstructed from measurement data), such as an MRI system, a CT system, an x-ray imaging system, an ultrasound imaging system, another medical imaging system, another computing device (e.g., a server storing image data or flow data), a flow simulation system, a PIV system, and so on. In some embodiments, flow data source 302 can be local to computing device 350. For example, flow data source 302 can be incorporated with computing device 350 (e.g., computing device 350 can be configured as part of a device for capturing, scanning, and/or storing images). As another example, flow data source 302 can be connected to computing device 350 by a cable, a direct wireless link, and so on. Additionally or alternatively, in some embodiments, flow data source 302 can be located locally and/or remotely from computing device 350, and can communicate data to computing device 350 (and/or server 352) via a communication network (e.g., communication network 354).

In some embodiments, communication network 354 can be any suitable communication network or combination of communication networks. For example, communication network 354 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CD MA, GSM, LTE, LTE Advanced, WiMAX, etc.), a wired network, and so on. In some embodiments, communication network 354 can be a local area network, a wide area network, a public network (e.g., the Internet), a private or semi-private network (e.g., a corporate or university intranet), any other suitable type of network, or any suitable combination of networks. Communications links shown in FIG. 3 can each be any suitable communications link or combination of communications links, such as wired links, fiber optic links, Wi-Fi links, Bluetooth links, cellular links, and so on.

Figure 4:
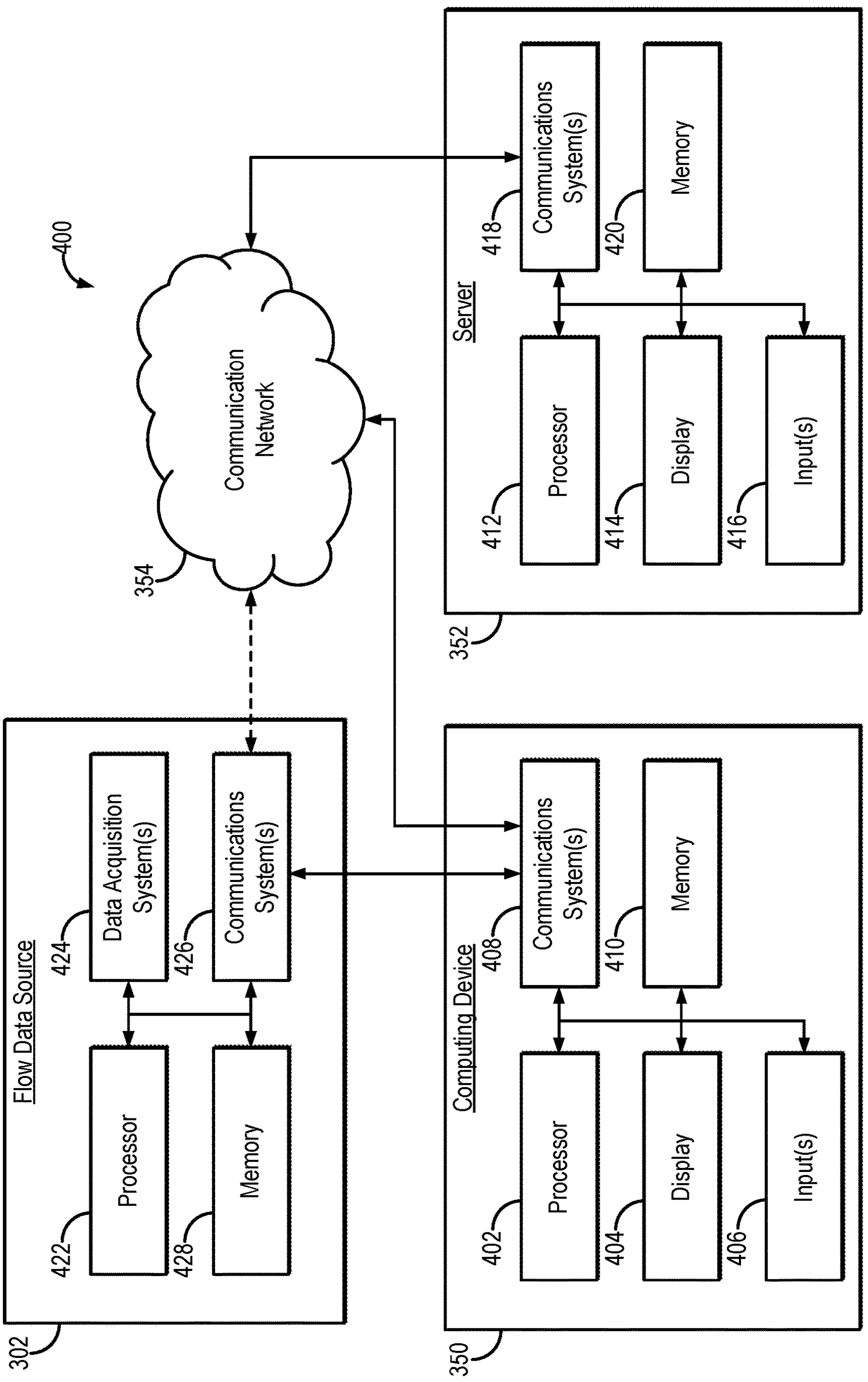
FIG. 4 is a block diagram of example hardware components implemented in the system of FIG. 3.

Referring now to FIG. 4, an example of hardware 400 that can be used to implement flow data source 302, computing device 350, and server 352 in accordance with some embodiments of the systems and methods described in the present disclosure is shown. As shown in FIG. 4, in some embodiments, computing device 350 can include a processor 402, a display 404, one or more inputs 406, one or more communication systems 408, and/or memory 410. In some embodiments, processor 402 can be any suitable hardware processor or combination of processors, such as a central processing unit ("CPU"), a graphics processing unit ("GPU"), and so on. In some embodiments, display 404 can include any suitable display devices, such as a computer monitor, a touchscreen, a television, a virtual reality ("VR") system, an augmented reality ("AR") system, and so on. In some embodiments, inputs 406 can include any suitable input devices and/or sensors that can be used to receive user input, such as a keyboard, a mouse, a touchscreen, a microphone, and so on.

In some embodiments, communications systems 408 can include any suitable hardware, firmware, and/or software for communicating information over communication network 354 and/or any other suitable communication networks. For example, communications systems 408 can include one or more transceivers, one or more communication chips and/or chip sets, and so on. In a more particular example, communications systems 408 can include hardware, firmware and/or software that can be used to establish a Wi-Fi connection, a Bluetooth connection, a cellular connection, an Ethernet connection, and so on.

In some embodiments, memory 410 can include any suitable storage device or devices that can be used to store instructions, values, data, or the like, that can be used, for example, by processor 402 to present content using display 404, to communicate with server 352 via communications system(s) 408, and so on. Memory 410 can include any suitable volatile memory, non-volatile memory, storage, or any suitable combination thereof. For example, memory 410 can include RAM, ROM, EEPROM, one or more flash drives, one or more hard disks, one or more solid state drives, one or more optical drives, and so on. In some embodiments, memory 410 can have encoded thereon, or otherwise stored therein, a computer program for controlling operation of computing device 350. In such embodiments, processor 402 can execute at least a portion of the computer program to present content (e.g., images, user interfaces, graphics, tables), receive content from server 352, transmit information to server 352, and so on.

In some embodiments, server 352 can include a processor 412, a display 414, one or more inputs 416, one or more communications systems 418, and/or memory 420. In some embodiments, processor 412 can be any suitable hardware processor or combination of processors, such as a CPU, a GPU, and so on. In some embodiments, display 414 can include any suitable display devices, such as a computer monitor, a touchscreen, a television, and so on. In some embodiments, inputs 416 can include any suitable input devices and/or sensors that can be used to receive user input, such as a keyboard, a mouse, a touchscreen, a microphone, and so on.

In some embodiments, communications systems 418 can include any suitable hardware, firmware, and/or software for communicating information over communication network 354 and/or any other suitable communication networks. For example, communications systems 418 can include one or more transceivers, one or more communication chips and/or chip sets, and so on. In a more particular example, communications systems 418 can include hardware, firmware and/or software that can be used to establish a Wi-Fi connection, a Bluetooth connection, a cellular connection, an Ethernet connection, and so on.

In some embodiments, memory 420 can include any suitable storage device or devices that can be used to store instructions, values, data, or the like, that can be used, for example, by processor 412 to present content using display 414, to communicate with one or more computing devices 350, and so on. Memory 420 can include any suitable volatile memory, non-volatile memory, storage, or any suitable combination thereof. For example, memory 420 can include RAM, ROM, EEPROM, one or more flash drives, one or more hard disks, one or more solid state drives, one or more optical drives, and so on. In some embodiments, memory 420 can have encoded thereon a server program for controlling operation of server 352. In such embodiments, processor 412 can execute at least a portion of the server program to transmit information and/or content (e.g., data, images, a user interface) to one or more computing devices 350, receive information and/or content from one or more computing devices 350, receive instructions from one or more devices (e.g., a personal computer, a laptop computer, a tablet computer, a smartphone), and so on.

In some embodiments, flow data source 302 can include a processor 422, one or more data acquisition systems 424, one or more communications systems 426, and/or memory 428. In some embodiments, processor 422 can be any suitable hardware processor or combination of processors, such as a CPU, a GPU, and so on. In some embodiments, the one or more data acquisition systems 424 are generally configured to acquire data, images, or both, and can include acquisition hardware for an MRI scanner (e.g., one or more radio frequency coils), a CT scanner (e.g., radiation detectors), an ultrasound system (e.g., an ultrasound transducer), and so on. Additionally or alternatively, in some embodiments, one or more data acquisition systems 424 can include any suitable hardware, firmware, and/or software for coupling to and/or controlling operations of the related acquisition hardware. In some embodiments, one or more portions of the one or more data acquisition systems 424 can be removable and/or replaceable.

Note that, although not shown, flow data source 302 can include any suitable inputs and/or outputs. For example, flow data source 302 can include input devices and/or sensors that can be used to receive user input, such as a keyboard, a mouse, a touchscreen, a microphone, a trackpad, a trackball, virtual reality glasses, a virtual reality system, an augmented reality system, and so on. As another example, flow data source 302 can include any suitable display devices, such as a computer monitor, a touchscreen, a television, etc., one or more speakers, and so on.

In some embodiments, communications systems 426 can include any suitable hardware, firmware, and/or software for communicating information to computing device 350 (and, in some embodiments, over communication network 354 and/or any other suitable communication networks). For example, communications systems 426 can include one or more transceivers, one or more communication chips and/or chip sets, and so on. In a more particular example, communications systems 426 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 428 can include any suitable storage device or devices that can be used to store instructions, values, data, or the like, that can be used, for example, by processor 422 to control the one or more data acquisition systems 424, and/or receive data from the one or more data acquisition systems 424; to images from data; present content (e.g., images, a user interface) using a display; communicate with one or more computing devices 350; and so on. Memory 428 can include any suitable volatile memory, non-volatile memory, storage, or any suitable combination thereof. For example, memory 428 can include RAM, ROM, EEPROM, one or more flash drives, one or more hard disks, one or more solid state drives, one or more optical drives, and so on. In some embodiments, memory 428 can have encoded thereon, or otherwise stored therein, a program for controlling operation of flow data source 302. In such embodiments, processor 422 can execute at least a portion of the program to generate images, transmit information and/or content (e.g., data, images) to one or more computing devices 350, receive information and/or content from one or more computing devices 350, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a flow metric map from medical flow data, the method comprising:

(a) accessing the medical flow data that depict blood flow measured non-invasively within a volume-of-interest of a subject's vasculature with a computer system;

(b) determining a reference point within the volume-of-interest of the medical flow data using the computer system;

(c) defining a virtual medical device representing an invasive medical device and having a virtual volume;

(d) constructing with the computer system, the virtual volume representing the virtual medical device as a subvolume within the volume-of-interest and defined based on the reference point;

(e) generating masked medical flow data with the computer system by masking the medical flow data using the virtual volume, the masked medical flow data representing a subset of the medical flow data in space corresponding to the virtual medical device;

(f) computing with the computer system, at least one flow metric based on the masked medical flow data; and (g) generating with the computer system, a flow metric map using at least one flow metric computed in step (f), wherein the flow metric map non-invasively characterizes the blood flow within the volume-of-interest of the subject's vasculature corresponding to the virtual medical device such that the characterized blood flow resembles blood flow that would be measured within the invasive medical device using invasive diagnostic catheterization and without altering the subject's vasculature.

2. The method of claim 1, wherein the virtual volume is constructed based on a distance measured relative to the reference point.

3. The method of claim 2, wherein the virtual medical device represents a catheter and the virtual volume is a tubular virtual volume and the distance measured relative to the reference point defines one or more radii.

4. The method of claim 3, wherein the reference point comprises a centerline of the volume-of-interest and the one or more radii are defined along a length of the centerline.

5. The method of claim 4, wherein the centerline comprises at least one of a single line segment, multiple line segments, or a plurality of points.

6. The method of claim 4, wherein the centerline comprises one or more line segments and at least one of the one or more line segments comprises at least one of a curvilinear line segment or a curve.

7. The method of claim 3, wherein the one or more radii consists of a single radius and the tubular virtual volume has a fixed radius defined by the single radius.

8. The method of claim 2, wherein the distance measured relative to the reference point is a non-Euclidean distance.

9. The method of claim 8, wherein the non-Euclidean distance is measured based on a geodesic distance transform.

10. The method of claim 2, wherein the distance measured relative to the reference point is a Euclidean distance.

11. The method of claim 10, wherein the Euclidean distance is measured based on a three-dimensional distance transform.

12. The method of claim 1, wherein the virtual volume is constructed using flow information contained in the medical flow data.

13. The method of claim 12, wherein the virtual volume is constructed based on thresholding the medical flow data, such that spatial regions represented in the medical flow data and the volume-of-interest are assigned to the virtual volume when a threshold criterion is satisfied.

14. The method of claim 12, wherein the flow information comprises at least one of one or more flow stream directions at one or more time points, one or more flow stream directions over a period of time, a magnitude of one or more flow paths at one or more time points, or a magnitude of one or more flow paths over a period of time.

15. The method of claim 12, wherein the virtual volume is constructed based on a region growing method in which flow data associated with the reference point are input as an initial seed for the region growing method.

16. The method of claim 15, wherein the virtual volume is constructed based on one of a single region or multiple regions.

17. The method of claim 1, wherein the reference point comprises an anatomical landmark within the volume-of-interest.

18. The method of claim 1, wherein the reference point comprises a flow descriptor within the volume-of-interest.

19. The method of claim 1, wherein the reference point comprises a geometric shape within the volume-of-interest.

20. The method of claim 19, wherein the geometric shape comprises a line.

21. The method of claim 20, wherein the line is a centerline of the volume-of-interest.

22. The method of claim 19, wherein the geometric shape comprises a plurality of connected line segments.

23. The method of claim 22, wherein the plurality of connected line segments comprises at least one of a curvilinear line segment or a curve.

24. The method of claim 19, wherein the geometric shape comprises a polygon.

25. The method of claim 1, wherein the reference point comprises a point within the volume-of-interest.

26. The method of claim 25, wherein the reference point comprises a center point of the volume-of-interest.

27. The method of claim 1, wherein the at least one flow metric comprises at least one of pressure gradient, pressure field, kinetic energy, energy loss, turbulent kinetic energy, flow velocity histogram, and flow pattern.

28. The method of claim 27, wherein the flow pattern comprises at least one of helicity, vorticity, vortex flow, or helical flow.

29. The method of claim 27, wherein the flow pattern comprises an organized flow pattern.

30. The method of claim 27, wherein the flow pattern comprises a disorganized flow pattern.

31. The method of claim 1, wherein the medical flow data comprise medical images acquired with a medical imaging system.

32. The method of claim 31, wherein the medical imaging system is at least one of a magnetic resonance imaging (MRI) system, an ultrasound system, or an x-ray computed tomography (CT).

33. The method of claim 1, wherein the medical flow data comprise computational flow dynamic (CFD) data.

34. The method of claim 1, wherein the medical flow data comprise particle image velocimetry data.

35. The method of claim 1, wherein the medical flow data are one-dimensional medical flow data.

36. The method of claim 1, wherein the medical flow data are multidimensional medical flow data.

37. The method of claim 1, wherein the flow metric map depicts the at least one flow metric at one or more time points, thereby enabling analysis of the at least one flow metric at one of a single time point, multiple time points, or over a period of time.

38. The method of claim 1, further comprising processing the flow metric map along one of a single flow direction or multiple flow directions.

39. The method of claim 1, further comprising segmenting the medical flow data with the computer system to generate a segmented volume corresponding to a region-of-interest, and wherein the volume-of-interest comprises the segmented volume such that the reference point is determined within the segmented volume and the virtual volume is constructed as a subvolume within the segmented volume and defined relative to the reference point.

40. The method of claim 39, wherein the segmented volume is generated by inputting the medical flow data to a trained mathematical model, generating output as the segmented volume.

41. The method of claim 40, wherein the trained mathematical model implements a trained machine learning algorithm.

42. The method of claim 41, wherein the trained machine learning algorithm implements a trained deep learning model.

43. A method for generating a virtual volume for analyzing medical flow data, the method comprising:

(a) accessing medical flow data that depict blood flow measured non-invasively within a volume-of-interest of a subject's vasculature with a computer system;

(b) determining a reference point within the volume-of-interest of the medical flow data using the computer system;

(c) defining a virtual medical device representing an invasive medical device and having a virtual volume;

(d) constructing with the computer system, the virtual volume representing the virtual medical device as a subvolume within the volume-of-interest and defined based on the reference point;

(e) generating masked medical flow data with the computer system by masking the medical flow data using the virtual volume, the masked medical flow data non-invasively representing a subset of the medical flow data in space corresponding to the virtual medical device such that the masked medical flow data characterize blood flow that would be measured within the invasive medical device using invasive diagnostic catheterization and without altering the subject's vasculature; and (f) storing the masked medical flow data as a data structure.

44. The method of claim 43, further comprising:

(g) computing with the computer system, at least one flow metric based on the masked medical flow data; and (h) generating with the computer system, a flow metric map using the at least one flow metric computed in step (g).

45. The method of claim 43, wherein determining the reference point comprises segmenting the medical flow data with the computer system to generate a segmented volume corresponding to the volume-of-interest and determining the reference point within the segmented volume using the computer system.

46. The method of claim 45, wherein the segmented volume is generated by inputting the medical flow data to a trained mathematical model, generating output as the segmented volume.

47. The method of claim 43, wherein the volume-of-interest is a vessel, and the virtual medical device is a virtual catheter having a tubular geometry; wherein determining the reference point within the vessel comprises determining a centerline through the vessel; and wherein constructing the virtual volume in step (c) comprises:

determining distances from the centerline to a lumen of the vessel based on the medical flow data;

defining a radius of the virtual catheter based on a percentile of the distances; and constructing the tubular virtual volume by measuring the radius from the centerline to define an outer extent of the tubular virtual volume, leaving a margin between the outer extent of the virtual volume and the lumen of the vessel.

48. A method for generating a flow metric map from medical flow data, the method comprising:

(a) accessing medical flow data with a computer system, wherein the medical flow data non-invasively depict blood flow within a volume-of-interest of a subject's vasculature;

(b) defining a virtual medical device representing an invasive medical device and having a virtual volume;

(c) constructing with the computer system, the virtual volume representing a virtual medical device as a subvolume within the volume-of-interest by inputting the medical flow data to a trained machine learning algorithm, generating output as the virtual volume;

(d) generating masked medical flow data with the computer system by masking the medical flow data using the virtual volume, the masked medical flow data representing a subset of the medical flow data in space corresponding to the virtual medical device;

(e) computing with the computer system, at least one flow metric based on the masked medical flow data; and (f) using the at least one flow metric map computed in step (e), generating with the computer system, a flow metric map non-invasively characterizing the blood flow within the volume-of-interest of the subject's vasculature, wherein the characterized blood flow resembles flow that would be measured within the invasive medical device using invasive diagnostic catheterization and without altering the subject's vasculature.

* * * * *